US005782383A

United States Patent [19]

Robinson

[11] Patent Number: 5,782,383

[45] Date of Patent: Jul. 21, 1998

[54] DISPENSING CLOSURE FOR SEALED ENTERAL FLUID CONTAINERS

[75] Inventor: Clayton L. Robinson, Newburgh, Ind.

[73] Assignee: Rexan Closures Inc., Evansville, Ind.

[21] Appl. No.: 706,253

[22] Filed: Sep. 4, 1996

[51] Int. Cl.$^{6}$ .............................. B67D 5/00; A61B 19/00; B65D 41/20

[52] U.S. Cl. .............................. 222/81; 222/80; 215/250; 604/405; 604/415

[58] Field of Search .............................. 222/81, 189.09

[56] References Cited

U.S. PATENT DOCUMENTS

| | | | |
|---|---|---|---|
| 2,186,908 | 1/1940 | Page et al. | 215/38 |
| 2,770,234 | 11/1956 | Nesset et al. | 128/214 |
| 2,812,117 | 11/1957 | Butkus et al. | 222/189 |
| 3,145,879 | 8/1964 | Williams | 222/212 |
| 3,293,773 | 12/1966 | Frazer et al. | 34/92 |
| 3,734,098 | 5/1973 | Schneller et al. | 128/272 |
| 3,746,001 | 7/1973 | Ralston, Jr. | 128/214 |
| 3,905,368 | 9/1975 | Lewis, Jr. et al. | 128/272 |
| 3,945,382 | 3/1976 | Ogle | 128/272 |
| 4,046,276 | 9/1977 | Winchell et al. | 215/250 |
| 4,053,648 | 10/1977 | Schmid et al. | 222/81 |
| 4,235,344 | 11/1980 | Kulle et al. | 215/250 |
| 4,301,799 | 11/1981 | Pope, Jr. et al. | 128/272 |
| 4,351,443 | 9/1982 | Uhlig | 215/216 |
| 4,375,864 | 3/1983 | Savage | 222/81 |
| 4,497,351 | 2/1985 | Garcia | 222/81 |
| 4,934,545 | 6/1990 | Pezzoli et al. | 215/250 |
| 4,981,464 | 1/1991 | Suzuki | 604/415 |
| 4,997,429 | 3/1991 | Dickerhoff et al. | 604/411 |
| 5,036,992 | 8/1991 | Mouchawar et al. | 215/307 |
| 5,165,578 | 11/1992 | Laible | 222/189.09 |
| 5,188,628 | 2/1993 | Rani et al. | 604/405 |

*Primary Examiner*—Andres Kashnikow
*Assistant Examiner*—Keats Quinalty
*Attorney, Agent, or Firm*—Gifford, Krass, Groh, Sprinkle, Patmore, et al.

[57] ABSTRACT

A dispensing closure for a sealed enteral fluid container includes a threaded cap with a central air inlet in the cap top covered by a hydrophobic/oleophobic air filter and an offset opening for a spike with an outwardly extending tubular spike guide. A resilient liner serves as a primary gasket seal between the cap top and the container neck lip and also seals to the spike during use while allowing air flow from the air inlet and filter along the spike into the container as enteral fluid is being withdrawn through the spike.

11 Claims, 3 Drawing Sheets

DISPENSING CLOSURE FOR SEALED ENTERAL FLUID CONTAINERS

BACKGROUND OF THE INVENTION

1. Field of the Invention

This invention relates to dispensing closures, and, more particularly, this invention relates to a removable closure for an enteral liquid container which includes a microbial air filter for introduction of clean air into the container as liquid is being withdrawn through a conventional spike cannula.

2. State of the Art

Closures for enteral fluid containers are typically provided with an outwardly extending cylindrical member having an opening to receive a piercing spike. In earlier versions, such as that shown in U.S. Pat. No. 4,235,344 to Kulle et al., it was considered necessary to seal the outward extending cylindrical member with a wall or membrane above the plane of the cap top or in the plane of the cap top itself, as shown in U.S. Pat. No. 4,934,545 to Pezzoli et al. Such a seal only has efficacy if the closure is used by itself to seal the container before it is spiked for use. Since the wall or membrane is molded integrally with the projecting cylindrical member or the cap top, once this wall or membrane is pierced by the spike, the closure will be prone to leakage between the spike or needle and the cap top. The gasket or liner supplied with these prior art structures is in the form of an annular disk or washer serving the sole function of sealing the container neck lip with the cap top; thus, leakage can occur between the spike and the hole it created.

U.S. Pat. No. 5,188,628 to Rani et al. shows a closure design to be applied to a container which has been filled and presealed with a pierceable member such as a metallic foil. The closure has a central spike receiving hole in its top with a cylindrical guide member. Four air apertures are spaced around the central spike hole and are covered by a hydrophobic air filter disk having a central spike hole. The disk is preferably located on the inside of the closure but may also be positioned over the apertures on the outside of the closure. In some instances the apertures may be covered by individual filters which may even lie within the apertures. The position of the filter is secured in the closure by any suitable means such as sonic welding. An internal disk shape cover having a thicker central portion is inserted into the closure over the filter. Preferably, the cover is adhesively sealed to the container neck foil seal by flowing a hot melt adhesive between the foil seal and the cover. The center portion of the internal cover is surrounded with a weakened area which is larger than the piercing spike so that the spike breaks but doesn't completely sever the weakened area, forming a hinged flap type structure producing an air path into the container. One of the difficulties with this structure is the creation of a leakage path for the container liquid since there is no sealing of the internal cover to the spike.

The hydrophobic air filter is often formed of a woven material, as indicated in the above-mentioned patent to Pezzoli et al. and apparently used in the structure of the above-mentioned patent to Rani et al. which mentions an air filter with the same trade name.

SUMMARY OF THE INVENTION

The dispensing closure of the present invention is designed to be used with a sealed enteral fluid container to accommodate piercing with a spike and the introduction of clean air to the container as liquid is being withdrawn through the spike. The present closure adopts the best features of the prior art, and improves or redesigns other features to overcome disadvantages previously encountered.

The closure includes a cap with a planar top and an annular skirt depending from the periphery of the top. The skirt contains neck engaging means usually in the form of an internal thread or a snap connection. The air inlet has been moved from the conventional offset location to a central location in the cap top where it is easiest to provide a sealing surface to which a hydrophobic-oleophobic microbial air filter is bonded. In a preferred embodiment of the invention, a single weld concentrator ring or two concentric weld concentrator rings project inwardly from the inside of the top surface surrounding the air inlet so that a tool may be introduced into the cap to fuse a filter disk to the cap top by melting the ring or rings.

The central air location also permits a simple liner configuration with a central aperture to provide a fluid reservoir not requiring alignment of the liner as would be required with an offset air inlet and reservoir location. Provision of a fluid reservoir over the air filter keeps the liquid product in contact with the filter during periods in which withdrawal is interrupted. This avoids clogging of the filter surface which would otherwise occur by allowing the filter to dry with a scum surface on it. It has been found that interruptions as short as three hours will allow the air filter to dry out without the reservoir, and such severe clogging of the filter can occur that upon resumption of liquid withdrawal the container collapses.

The spike receiving opening is located in the cap top offset from the center, between the air inlet and the annular cap skirt, with an outwardly extending tubular spike guide aligned with the opening. At this offset position, the spike will penetrate the container sealing member or foil at a more taut position than if the spike hole is located at the cap center. For example the foil over the container neck can dip at the center due to the negative pressure within the container. This taut condition of the foil in combination with a resilient liner allows the spike to push and stretch the liner material between the spike and foil providing an air passage between the spike and foil around the entire circumference of the spike.

The sealing liner is in the form of a circular disk having an outside diameter equal to the inside diameter of the cap skirt so that when the liner is inserted into the cap before capping the container, the liner will be retained by an inwardly directed projection or bead above the cap thread and adjacent the cap top. When the cap is threaded on the container neck, the liner will provide the primary seal between the inside of the cap top and the lip of the container neck.

The sealing liner has a central aperture approximately the same size as the air inlet in the cap top and the same size or slightly smaller than the air filter bonded to the cap top. This provides the above-mentioned fluid reservoir and direct ingress to the air filter and air opening in the cap top.

The liner is a resilient material which stretches and yields as the spike pierces the liner and foil, drawing the liner along the spike to push the foil away from the spike providing a fluid passage between the member and the liner and along the periphery of the spike into the container allowing filtered air to enter the container as container liquid is being dispensed through the spike, and if dispensing is stopped for a period of time, allowing flow of container liquid to the reservoir to keep the air filter wet. With the spike hole being offset from the center of the cap top, the foil will be tighter and closer to the liner, requiring less stretching of the liner to break through between the foil and the spike.

It has been determined that the best liner material is manufactured from a resilient thermoplastic such as PP, polypropylene, or EVA, ethyl vinyl acetate, in the form of a thick foam core between two solid layers of the same material. Many materials such as polyethylene cannot be used for the liner because they are not resilient enough and tend to break up before a satisfactory stretch has been reached.

BRIEF DESCRIPTION OF THE DRAWING

The advantages of the present invention will be more apparent from the following detailed description when considered in connection with the accompanying drawing wherein.

DETAILED DESCRIPTION OF THE PREFERRED EMBODIMENT

Figure 1:
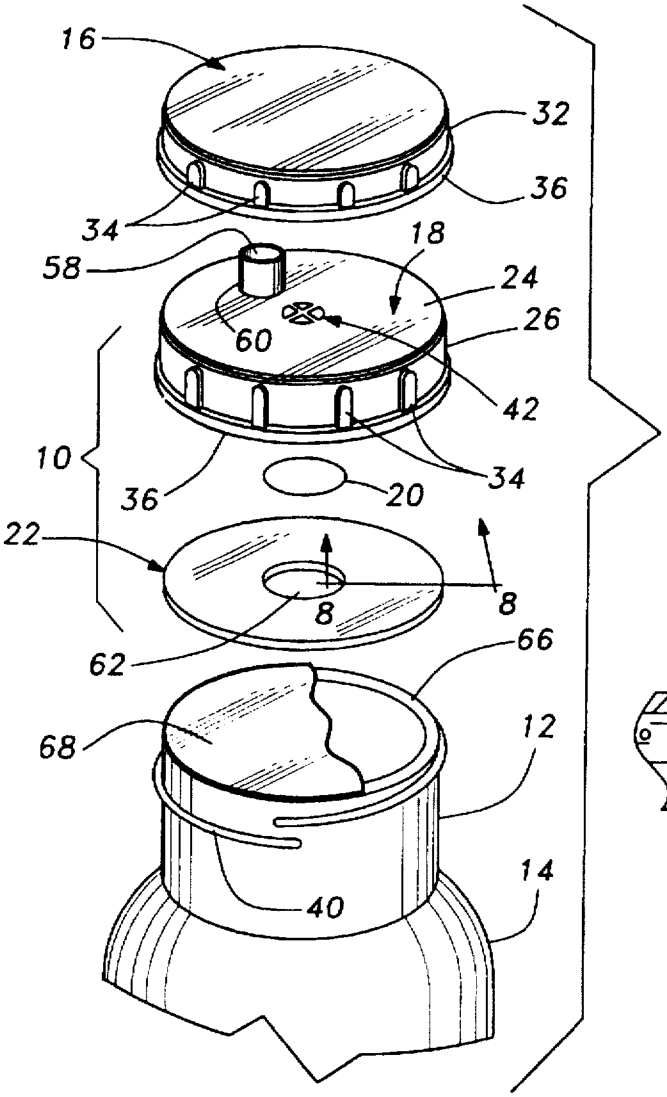
FIG. 1 is an exploded perspective view of the closure including a cap, an air filter and a sealing liner with a dust cover which attaches to the closure and the container with a sealing member such as a foil bonded to its neck lip.

Referring to FIG. 1, the closure 10 of this invention is shown as it is applied to the neck 12 of a container 14 containing an enteral feeding liquid. A dust cover 16 snaps onto the top of the closure to protect the top orifices from the environment.

Figure 2:
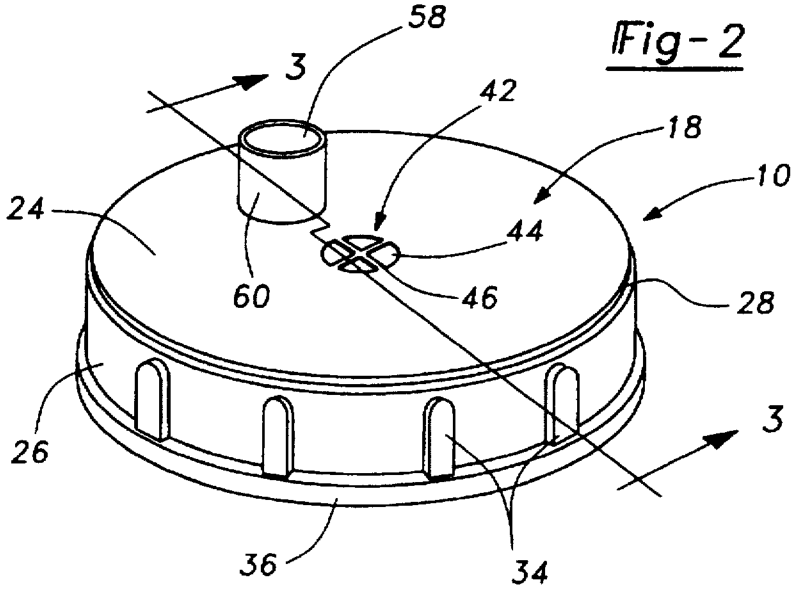
FIG. 2 is a enlarged perspective view of the closure.
Figure 3:
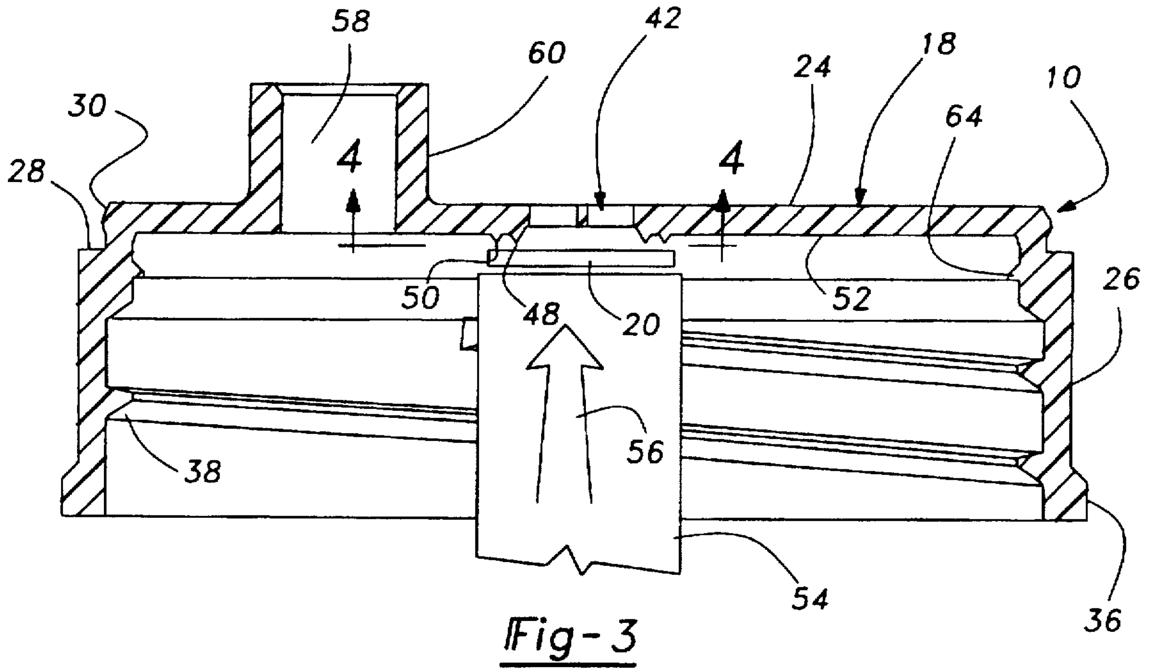
FIG. 3 is a cross-sectioned elevational view of the closure taken along line 3—3 of FIG. 2 before air filter is bonded to the inside of the cap top.

As seen in FIGS. 1–3, the closure 10 includes a cap 18, an air filter 20 and a resilient sealing liner 22. The cap 18 has a planar top 24 with an annular cap skirt 26 depending from its peripheral edge. An undercut 28 and shallow outwardly extending bead 30 at the juncture of the top 24 and skirt 26 serve to secure the annular skirt 32 of the dust cover 16 to and in line with the cap skirt 26. The dust cover 16 has a shallow inwardly directed bead, not shown, at the bottom of its skirt 32 which snaps over the cap bead 30. The cap skirt 26 and the dust cover skirt 32 have a knurl comprising a series of circumferentially spaced axially extending ribs 34 to assist the user in gripping the dust cover and cap. Both the dust cover and cap can also have an outward extending scuff band 36 located at the bottom of their respective skirts. The cap skirt 26 has an internal thread 38 which engages a complementary external thread 40 on the container neck 12. The cap and dust cover are injection molded with a suitable thermal plastic material such as polypropylene.

Figure 4:
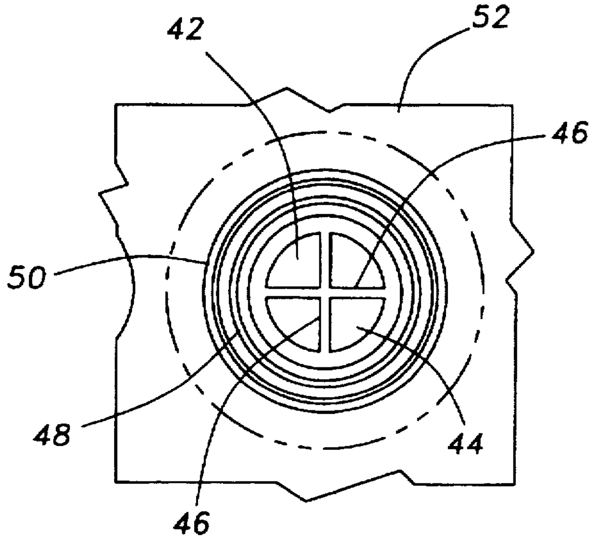
FIG. 4 is a plan view taken along line 4—4 of FIG. 3.

The cap top 24 has a centrally located air opening or orifice 42 preferably provided with molded intersecting diametrical ribs 44 which serve as a protective grid and support for the air filter 20. The ribs divide the air opening into quadrant sections 46 as best seen in FIGS. 2 and 4.

The air filter 20, commonly referred to as a microbial filter, is designed to be an airborne bacteria barrier to admit clean air to the container as the liquid content of the container is being evacuated. The filter must allow the passage of air while blocking the flow of a water or oil based liquid; thus, the material must be both hydrophobic and oleophobic. We have found a non-woven cellulose fiber on a glass filter matrix bonded and treated with an oleophobic-hydrophobic formulation as well as a polymer binder to be excellent. Such a material may be obtained from Pallflex Products Company of Putnam, Conn.

Figure 5:
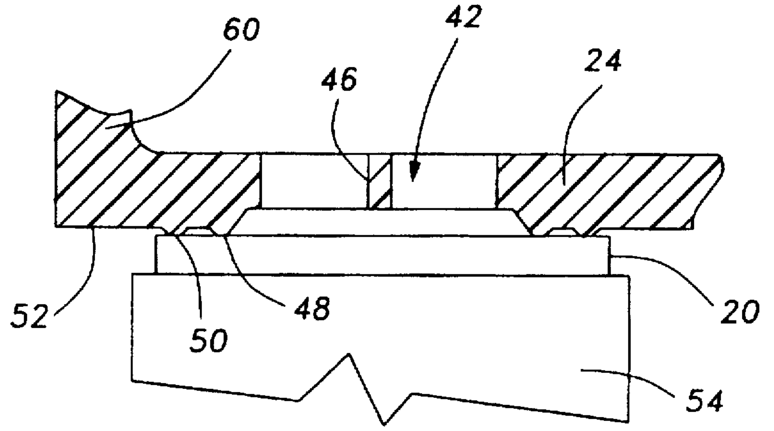
FIG. 5 is an enlarged partial view of the cap top as the air filter is being bonded to the inside of the cap top.

It has been determined that the most effective use of the air filter is obtained when it is bonded directly to the inside of the cap top. This is accomplished by providing concentric weld concentrator rings 48 and 50 surrounding the air inlet 42 and projecting downwardly from the inside cap top surface 52 as shown in FIG. 3. The air filter 20 is bonded to the inside surface 52 by introducing a sonic welding probe 54 into the cap as shown by direction arrow 56 in FIG. 3. The probe 54 presses the filter disk 20 against the rings 48 and 50, melting them to bond the filter to the cap top as shown in FIG. 5.

The cap top 24 is provided with a spike receiving opening 58 which is surrounded by an outwardly extending tubular guide 60. The opening 58 and the guide 60 are offset between the central air opening 42 and the cap skirt 26. The bore or inside diameter of the guide 60 is sized to form a seal with the normal taper of the spike 74.

Resilient sealing liner 22 shown in FIGS. 1 and 6–8 has a circular perimeter and diameter to fit into cap skirt 26 pushing past internal cap thread 38 to be retained in the cap by inwardly projecting retention flange 64. The liner 22 also has a central aperture 62 of approximately the same size or slightly larger than the air filter 20 and cap top air inlet 42.

One of the primary functions of the sealing liner 22 is to serve as a sealing gasket between the closure 10 and the container 14 by being compressed between the inside cap top surface 52 and the container neck lip 66. When the container 14 is filled with its enteral feeding solution, it is heat sealed with a pierceable member most commonly in the form of an aluminum foil 68, so that sealing to lip 66 embraces the foil 68 and its seal to the lip 66. The liner 22 must have the usual gasket resiliency to accommodate various degrees of compression occurring when the closure is tightened on the container neck and even repeated compression, should the closure be loosened or removed and reapplied and sealed. Furthermore, the sealing properties cannot be adversely affected by sterilization or an autoclaving procedure.

Figure 8:
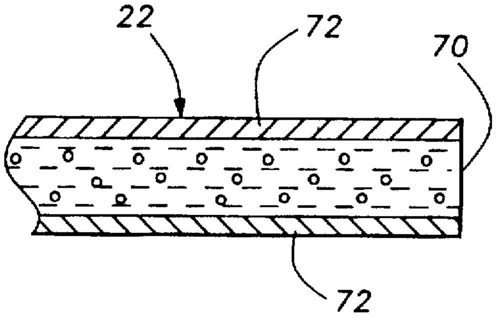
FIG. 8 is a sectional view taken along line 8—8 in FIG. 1 showing the tri-layer structure of the sealing liner.

Additionally, the liner must have an internal resilience not only to withstand puncture by spike for fluid removal from the container, but it must serve a new function of stretching between the needle or spike and the container neck sealing member or foil to provide an air path into the container from the air filter as fluid is withdrawn through the spike. Finally, it must provide a seal to the spike to prevent leakage during use. It has been found that this can be accomplished with a three layer laminate structure employing a central thick foamed thermal plastic material between two thinner solid layers of thermal plastic material. The overall thickness can be a nominal .040" or/preferably/between.035 and .050". A three-ply coextruded material of a foamed copolymer between two solid layers of the same copolymer appears to be an ideal structure. We have found that the resiliency offered by a polypropylene or EVA, ethyl vinyl acetate is best and that other materials such as polyethylene are not resilient enough to withstand sufficient stretch to move between the needle and the foil without fracturing. As seen in FIG. 8 which is a cross-section of the liner 22, the central core layer 70 is a foam which is between the two outside solid layers 72.

Figure 6:
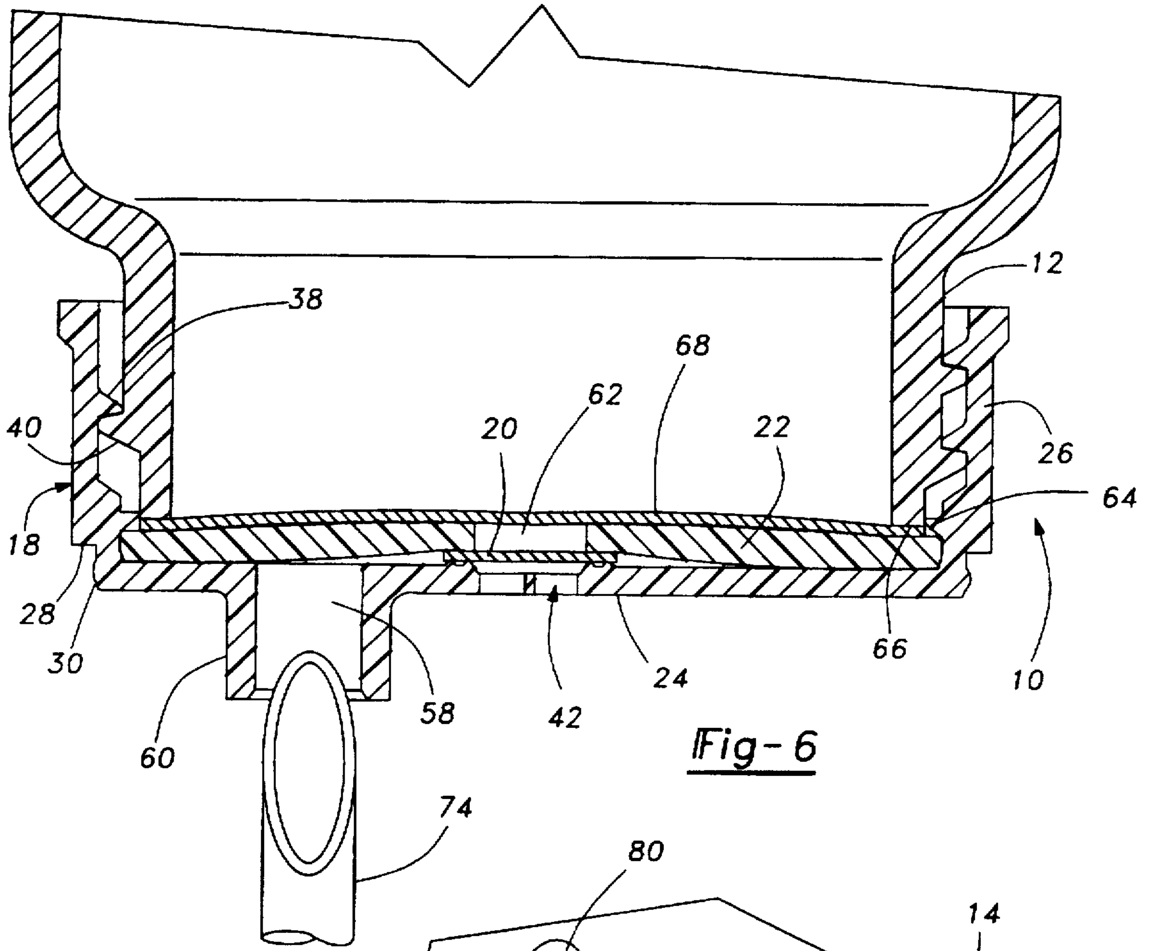
FIG. 6 is a cross-sectioned elevational view of the closure container package in its inverted use position as it will receive the spike for emptying the liquid content of the container.

As seen in FIG. 1, the container neck 12 is sealed with a foil 68 bonded to its lip 66. In FIG. 6, the cap 18 is shown sealed to the container lip 66 by the liner 22 and in its inverted position to receive spike 74 through guide 60 and spike receiving opening 58 in cap top 24.

Figure 7:
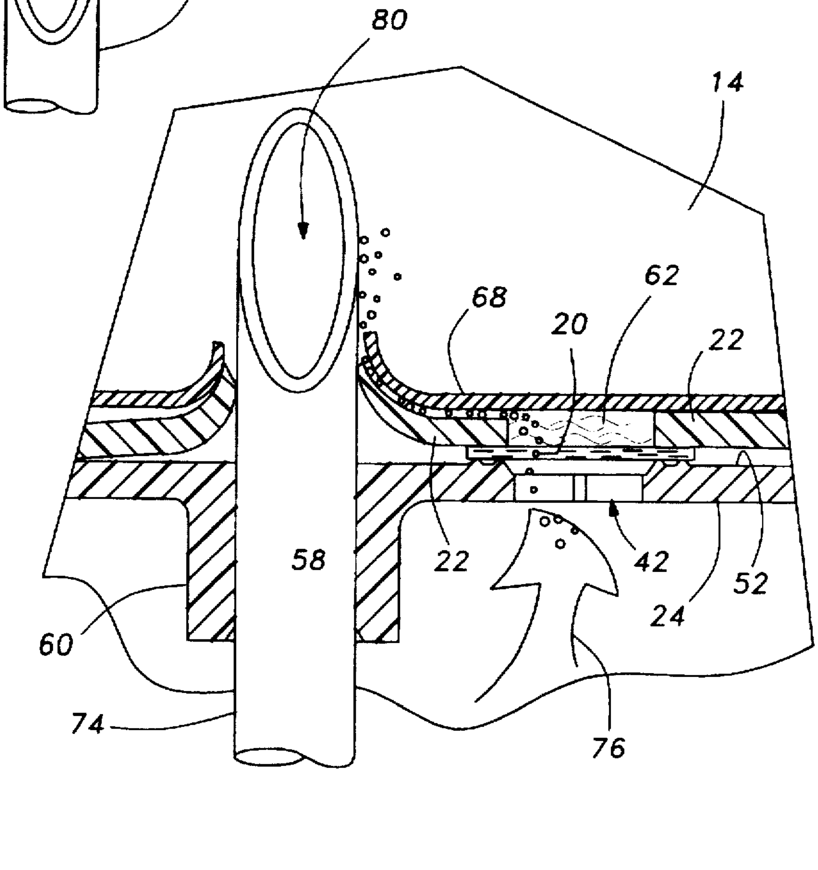
FIG. 7 is an enlarged sectional view of a portion of the cap top showing the penetration of the spike through the cap top, liner and foil and further showing the air path for introducing the air into the container as the liquid is being withdrawn.

FIG. 7 shows the spike 74 pushed through the cap top opening 58, piercing first the liner 22 and then the foil 68, causing the liner to move between the spike 74 and the foil 68 opening an air path along the spike 74 into the container 14 by pushing the foil 68 away from the spike 74 and at the same time allowing the liner 22 to seal against the spike 74 preventing liquid leakage. The air path is shown by the arrow 76 and the depicted air bubbles to be from outside the container and closure, through the air opening 42 in the cap top 24 and the air filter 20, through the central opening 62 in the liner 22 to the space between the liner 22 and foil 68 into the container. The initial puncture allows the container liquid to fill the liner opening 62 below the foil 68 which acts as a liquid reservoir above the liquid impervious air filter 20 which will keep this air filter wet and unclogged even if the liquid withdrawal from the container through the spike, as shown by the arrow 80, is temporarily disrupted. During the time of disruption, liquid can flow from the container along the air path to the reservoir to keep it filled with liquid.

I claim:

1. A dispensing closure for connection to the neck of a liquid container, the neck having a lip defining a fluid opening with a pierceable member covering the lip and sealing the fluid opening, said closure comprising:

a cap having a planar top and an annular skirt depending from the periphery of said top, said skirt having means for engaging said closure neck;

said top having an air opening formed in a central portion of said top a spike guide on said cap forming a spike receiving opening offset from said central portion of said top toward said annular skirt;

an air filter covering said air opening and bonded to an inside surface of said top around said air opening;

a resilient sealing liner abutting an inner surface of said cap top, said liner having an aperture aligned with said air opening;

whereby when said closure is engaged with said container neck, sealing occurs between the liner and the pierceable member covering the lip of said container neck and between the liner and the inside surface of said top;

when said liner and said member being pierced said container is inverted for dispensing, and a spike is inserted through said spike guide, pierced portions of said liner being deflected and drawn along with said spike, to push the pierced portion said member away from said spike and said liner to provide a fluid passage between said member and said liner and along said spike into said container, allowing filtered air to enter said container as container liquid is being dispensed through said spike and allowing flow of container liquid to said air filter to keep said air filter wet when dispensing is stopped for a period of time.

2. The closure according to claim 1 wherein said means for engaging said closure neck includes an internal thread on said annula skirt for engaging a threaded container neck.

3. The closure according to claim 2 including an inwardly directed projection on said cap annular skirt between said thread and cap top for retaining said liner in the cap prior to assembly of said closure to a container.

4. The closure according to claim 1 wherein said air opening is centrally located in said top and the aperture in said liner is centrally located, and wherein when said container is inverted and pierced for dispensing, said centrally located aperture in said liner acts with said pierceable member, and filter to form a reservoir for container liquid.

5. The closure according to claim 4 wherein said air inlet is formed as a circular orifice divided by intersecting diametrical ribs.

6. The closure according to claim 4 wherein said air filter is bonded to the cap top by melting a weld concentrator ring surrounding said air opening and projecting from said inside top surface.

7. The closure according to claim 1 wherein said air filter is a non-woven fibrous material treated to be hydrophobic and oleophobic.

8. The closure according to claim 1 wherein said liner is made with a three-ply thermal plastic material having a central foam layer and solid outer layers.

9. The closure according to claim 8 wherein said liner is a three ply coextruded material having a foamed polymer core between two solid layers of the same polymer.

10. The closure according to claim 9 wherein said polymer material is a polypropylene.

11. The closure according to claim 1 further including a dust cover removably attached to said cap, covering said spike guide and air opening.

* * * * *